(12) United States Patent
Tanaka (10) Patent No.: US 8,021,423 B2
(45) Date of Patent: Sep. 20, 2011

(54) INTRAOCULAR LENS INSERTION TOOL

(75) Inventor: Masayoshi Tanaka, Nagoya (JP)

(73) Assignee: Kowa Company, Ltd., Nagoya (JP)

( * ) Notice: Subject to any disclaimer, the term of this patent is extended or adjusted under 35 U.S.C. 154(b) by 160 days.

(21) Appl. No.: 12/309,829

(22) PCT Filed: Jul. 5, 2007

(86) PCT No.: PCT/JP2007/000733
§ 371 (c)(1),
(2), (4) Date: Feb. 10, 2009

(87) PCT Pub. No.: WO2008/018163
PCT Pub. Date: Feb. 14, 2008

(65) Prior Publication Data
US 2009/0292294 A1 Nov. 26, 2009

(30) Foreign Application Priority Data
Aug. 11, 2006 (JP) .................................. 2006-220648

(51) Int. Cl.
*A61F 2/16* (2006.01)

(52) U.S. Cl. ........................................ 623/6.12; 606/107

(58) Field of Classification Search ................. 606/107; 623/6.11, 6.12
See application file for complete search history.

(56) References Cited

U.S. PATENT DOCUMENTS

| | | | |
|---|---|---|---|
| 6,605,093 B1 * | 8/2003 | Blake | 606/107 |
| 6,629,979 B1 * | 10/2003 | Feingold et al. | 606/107 |
| 6,712,848 B1 * | 3/2004 | Wolf et al. | 623/6.12 |
| 2001/0007075 A1 | 7/2001 | Hjertman et al. | |
| 2002/0165610 A1 * | 11/2002 | Waldock | 623/6.12 |

FOREIGN PATENT DOCUMENTS

| | | |
|---|---|---|
| JP | A-11-506357 | 6/1999 |
| JP | A-2002-525023 | 8/2002 |
| JP | B2-3420724 | 4/2003 |
| JP | A-2003-515387 | 5/2003 |
| WO | WO 96/25101 | 8/1996 |
| WO | WO 96/28122 | 9/1996 |
| WO | WO 2005/070341 A1 | 8/2005 |
| WO | WO 2006/080191 A1 | 8/2006 |

* cited by examiner

*Primary Examiner* — Ryan Severson
(74) *Attorney, Agent, or Firm* — Oliff & Berridge, PLC (57) ABSTRACT

An insertion tool of an intraocular lens permits the lens to be deformed while rotation of the lens in an insertion tube is effectively prevented. Upper and lower flat planes are formed to spread flatly over a length of a through hole in the insertion tube and the upper and lower flat planes are connected smoothly with right and left wall faces over the length of the through hole. The right and left wall faces have longitudinal linear portions extending substantially in parallel in a vertical direction on a proximal end opening side. With its radius of curvature decreasing gradually in a covered shape which becomes inwardly concave as it approaches a distal end opening the upper flat plane gradually approaches the lower flat plane, and a tapered portion having a reduced cross-sectional area is formed, thus obtaining the distal end opening of substantially oval shape.

6 Claims, 9 Drawing Sheets

INTRAOCULAR LENS INSERTION TOOL

TECHNICAL FIELD

The present invention relates to an intraocular lens insertion tool used to insert an intraocular lens into the eye.

BACKGROUND ART

One method employed in the past in the field of cataract surgery involves extracting the intracapsular crystalline lens through a surgical incision made in ocular tissue such as the cornea (sclera) or anterior capsule section of the crystalline lens, and once the crystalline lens has been removed, inserting an intraocular lens serving as a replacement for the crystalline lens back through the incision and positioning it within the capsule.

Particularly in recent years, methods that employ an intraocular lens insertion tool like that disclosed in Patent Document 1 and Patent Document 2 have come into widespread use. Typically, the intraocular lens will be inserted into the eye by first inserting the distal orifice of an insertion tube provided at the distal end section of the body of the tool through a surgical incision, then pushing the intraocular lens (which has been maintained in a state of compact deformation inside the body of the tool) out through the distal orifice of the insertion tube.

By employing such an insertion tool, the intraocular lens can be inserted into the eye without expanding the surgical incision that was made for the purpose of extracting the crystalline lens, thereby reducing the labor entailed in the surgical operation, as well as reducing the risk of post-surgical astigmatism or infection.

Problems encountered with such conventional insertion tools include a tendency for the intraocular lens to rotate inside the insertion tube or to flip front to back as the intraocular lens is pushed along.

In order to deal with such problems, there has been proposed in Patent Document 3, for example, an insertion tool in which the shape of the inside face of the insertion tube is a discontinuous shape having an inflection point, designed so that the intraocular lens becomes lodged at the inflection point so as to prevent it from rotating.

However, an insertion tool constructed in this manner poses a risk that due to becoming lodged in this way, the intraocular lens may experience unnecessary bending or be subjected to localized action of excessive levels of deformation or stress. For this reason, the insertion resistance of the intraocular lens will be greater, with an attendant risk or deformation or damage when forcibly pushed. An additional difficulty is the problem, in terms of the mold etc., of forming an inflection point having a sufficiently acute angle to hold up the intraocular lens and prevent it from rotating.

Patent Document 1: JP-A-2002-525023
Patent Document 2: JP-A-11-506357
Patent Document 3: Japanese Patent No. 3420724

DISCLOSURE OF THE INVENTION

Problem the Invention Attempts to Solve

With the foregoing in view, it is an object of the present invention to provide an intraocular lens insertion tool of novel construction adapted to minimize deformation of the intraocular lens, while effectively preventing the intraocular lens from rotating inside the insertion tube.

Means for Solving the Problem

The modes of the present invention addressed to solving the aforementioned problems will be discussed below. The constituent elements employed in the various modes may be employed in any possible combination.

Specifically, the present invention resides in an intraocular lens insertion tool including a tool body having generally tubular shape for accommodating an intraocular lens, and a plunging member inserted into the tool body from a rear in an axial direction and moved forward for inserting into an eye the intraocular lens such that the intraocular lens undergoes compact deformation in association with forward displacement in the axial direction by the plunging member and is pushed out, characterized in that: an insertion tube disposed at a distal end section of the tool body and adapted for insertion into the eye, viewed perpendicular to a direction of extension thereof, has across an entire length from a proximal end opening to a distal end opening of the insertion tube a cross section wherein an upper and lower portions have traverse linear portions that extend substantially parallel in a width direction, and left and right portions that connect smoothly with the upper and lower portions; that in at least one part of the insertion tube in the direction of extension towards the proximal end opening, the left and right portions have longitudinal linear portions that extend substantially parallel in a vertical direction; and that the upper and lower portions gradually approach one another due to a radius of curvature that decreases gradually in an inwardly concave curved shape towards the distal end opening to form a tapered portion having a reduced cross-sectional area, thus producing the distal end opening of substantially oval shape.

In the intraocular lens insertion tool constructed according to the present invention, the intraocular lens can be pushed along in the forward direction while preventing it from rotating in the circumferential direction of the insertion tube. Specifically, in an insertion tube having a specific shape like that taught in the present invention, the center section of the intraocular lens can initially be positioned stably at the proximal end opening by being clamped against a wide zone of a flat portion defined by the traverse linear portion of the lower plane. The intraocular lens will be stably clamped against the lower plane from above by the curved shape of the left and right planes. Due to the flat plane formed on the upper plane as well, clamping force will be directed onto the intraocular lens in such a way as to be substantially free from associated rotative force in the circumferential direction. Further, because the dimensions of the left and right planes become smaller towards the distal end, if for example the intraocular lens should begin to experience rotational displacement to one side on the circumferential of the insertion tube, reaction force on one side will no longer equal reaction force on the other side, making it possible to achieve a spontaneous return mechanism back to the initial state.

According to the intraocular lens insertion tool of the present invention, the left and right planes inside the insertion tube connect to the upper and lower planes smoothly through common tangents with no inflection point. Thus, even if the intraocular lens should happen to experience displacement in the circumferential direction of the insertion tube, it will be possible to prevent localized excessive force from being exerted on the intraocular lens, and to prevent as much as possible deformation or damage to the intraocular lens.

In the present invention, the tapered portion may be formed in at least a portion of the insertion tube. It would therefore be acceptable, for example, to form a tube portion that extends in a straight line further towards the distal end opening from the distal end portion of the tapered portion.

Additionally, in a preferred mode of the intraocular lens insertion tool of the present invention, the cross section of the insertion tube viewed perpendicular to the direction of extension will become gradually smaller towards the tapered portion across the entire length from the proximal end opening to the distal end opening of the insertion to be, so that the tapered portion is formed across the entire length of the insertion tube. With this arrangement, the length dimension of the insertion tube can be used effectively to bring about deformation of the intraocular lens to smaller size.

In another preferred mode of the intraocular lens insertion tool of the present invention, wherein as viewed in cross section in a direction of extension, the lower portion of the tapered portion has a linear shape, whereas the upper portion has an inwardly convex, arcuate curved portion of substantially unchanging curvature which gradually approaches the lower portion towards the distal end opening. With this arrangement, the intraocular lens can be deformed more smoothly while being clamped stably against the lower plane.

In yet another preferred mode of the intraocular lens insertion tool of the present invention, the tool body has a stage at approximately center section in the axial direction thereof, the stage being open at a top and adapted for the intraocular lens to rest thereon; an upwardly open recessed groove is formed on the stage so as to extend in the axial direction of the insertion tube and communicates with the proximal end opening; and a cover member is provided to close an opening of the stage, and has a clamping projection adapted to clamp the intraocular lens resting on the stage from above and to compress the intraocular lens into the recessed groove in an upwardly concave curved state so that the intraocular lens is pushed in a curved state into the insertion tube.

With this arrangement, the intraocular lens can be rested easily in the tool body. Then, by compressing the intraocular lens resting on the stage from above with the clamping projection, the intraocular lens can be steadily deformed to upwardly concave shape while being clamped against the lower plane of the recessed groove. Thus, steady initial deformation of the intraocular lens when pushed into the insertion tube can be achieved with excellent control, making it possible for deformation of the intraocular lens inside the insertion tube to take place more steadily and smoothly.

EXPLANATION OF NUMERALS

10: intraocular lens insertion tool, 12: tool body, 14: plunger member, 22: through hole, 23: proximal end opening, 24: distal end opening, 25: upper flat plane; 26: lower flat plane, 28: left wall face, 30: right wall face, 32: intraocular lens, 34: rest portion, 44: cover portion, 62: pedestal portion, 64: projecting plate portion, 83: flat portion, 84: sloped portion, 130: through hole, 132: inflection portion, 140: through hole, 142: tapered portion, 144: straight portion

BEST MODE FOR CARRYING OUT THE INVENTION

In order to provide a more specific understanding of the present invention, preferred embodiments of the invention will be discussed in detail below with reference to the accompanying drawings.

Figure 1:
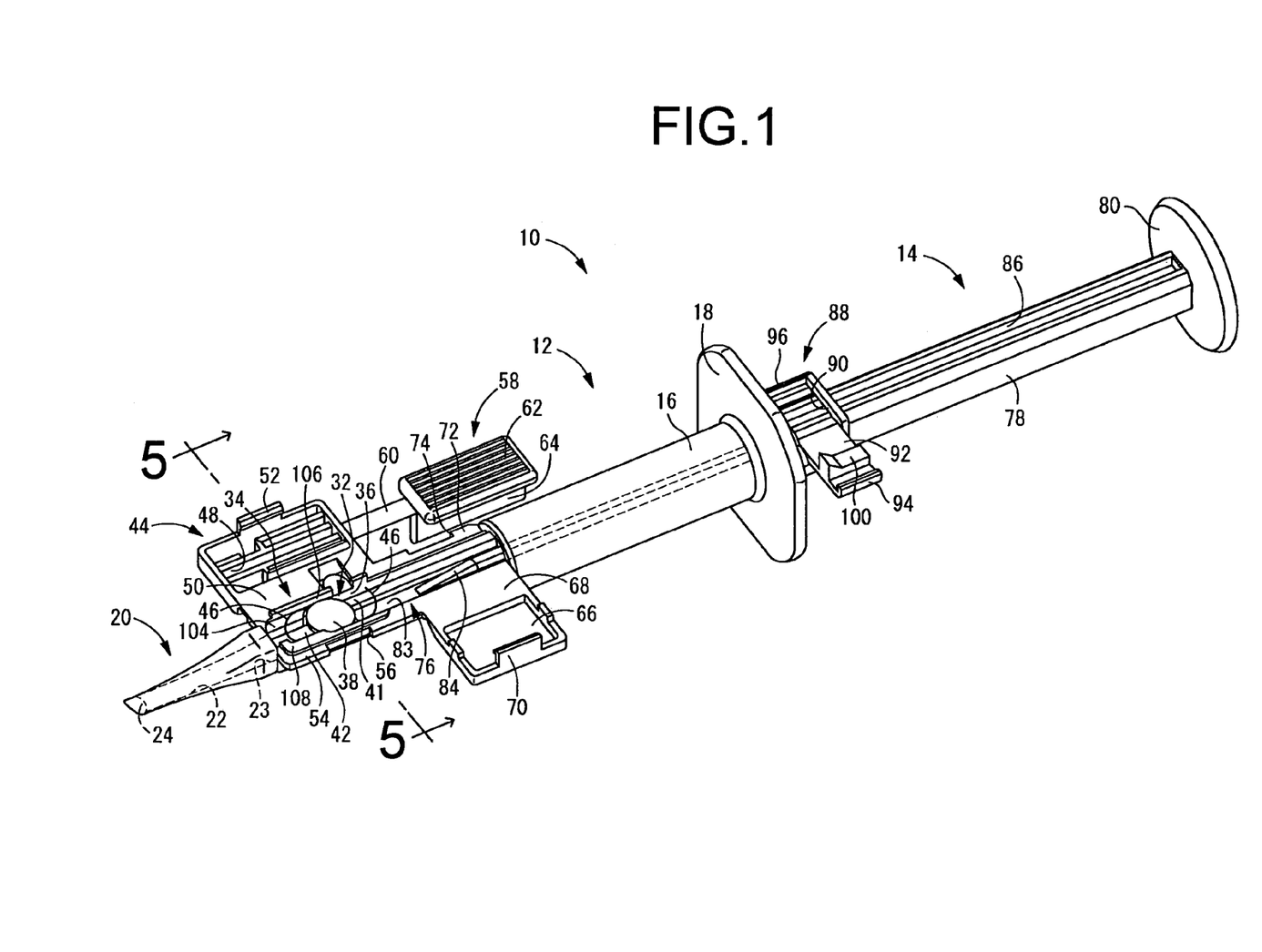
FIG. 1 is a perspective view of an intraocular lens insertion tool of construction according to one embodiment of the invention.

First, an intraocular lens insertion tool 10 according to a first embodiment of the present invention is depicted in FIG. 1. The insertion tool 10 includes a tool body 12 having generally tubular shape perforated in its interior throughout its entire length and open at the front and back ends, into which inserts a plunger 14. Herein, 'front' refers to the direction of extension of the insertion tool 10 (leftward in FIG. 1), and 'upward' refers to the upward direction in FIG. 1. 'Left-right direction' refers to the left-right direction of the insertion tool 10 in rear view (in FIG. 1, the lower right side is left and the upper left side is right).

The tool body 12 has a main tubular section 16 of generally round tubular shape, and at the back end of the main tubular section 16 there is integrally constituted a plate portion 18 of oblong shape extending in a plane perpendicular to the direction of extension of the main tubular section 16.

Figure 2:
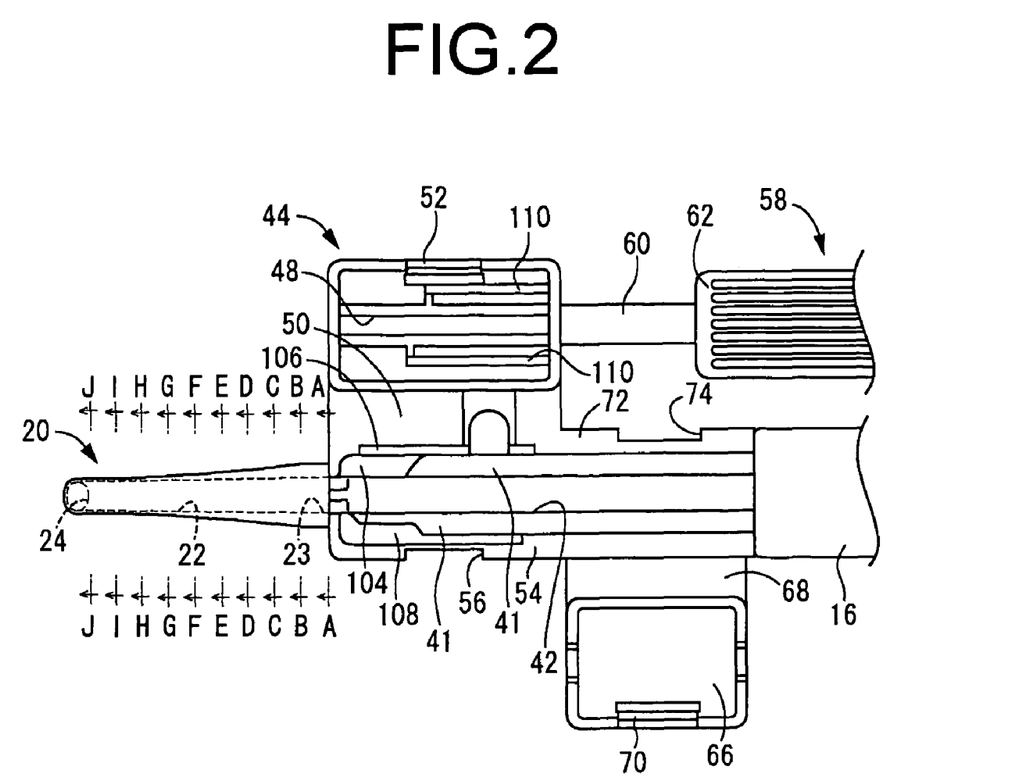
FIG. 2 is a top plane view of a primary part of the intraocular lens insertion tool.
Figure 3:
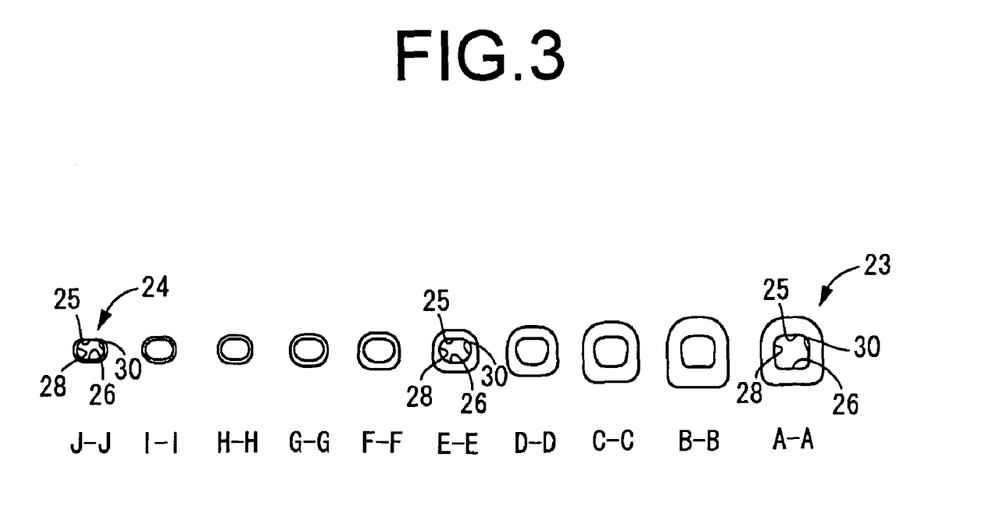
FIG. 3 is a cross sectional view taken along lines A-A to J-J of FIG. 2.

Meanwhile, at the distal end of the tool body 12 there is integrally formed a nozzle part 20 provided as the insertion tube. As depicted in FIGS. 2 and 3, the nozzle part 20 is formed to have outside contours that gradually taper towards the distal end in the direction of extension from the proximal end of the tool body 12. A through hole 22 is formed extending through the entire length of the nozzle part 20 in the direction of its extension. As depicted in FIG. 3, the through hole 22 has a generally oblong opening shape at its proximal end opening 23 at the proximal end (cross section A-A in FIG. 3), and gradually changes in shape to a generally oval shape towards its distal end opening 24 on the distal end side (cross section J-J in FIG. 3).

To describe in more detail, at the proximal end opening 23 side, the through hole 22 has upper and lower flat planes 25, 26 provided as flat traverse linear portions that extend substantially parallel in the width direction on the upper and lower planes; and left and right wall faces 28, 30 provided as flat longitudinal linear portions that extend substantially parallel in the vertical direction on the left and right planes and connect with the edges of the upper and lower flat planes 25, 26 to define an opening of generally oblong shape. The traverse direction extension dimensions of the upper and lower flat planes 25, 26 become gradually smaller towards the distal end opening 24. At the same time, the left and right wall faces 28, 30 gradually curve in an inwardly concave direction at progressively smaller curvature radius towards the distal end opening 24, thus becoming gradually smaller in height and producing a generally arcuate shape at the distal end opening 24.

Figure 4:
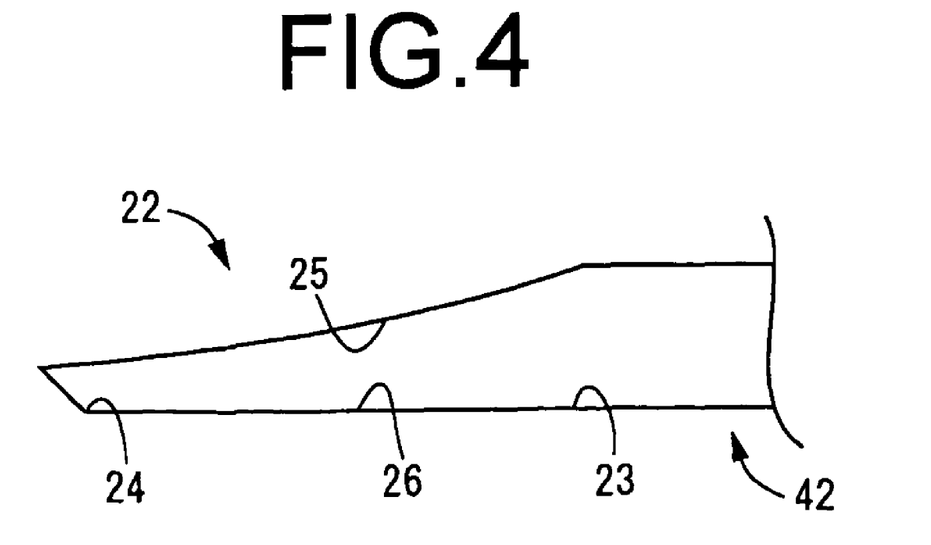
FIG. 4 is a vertical cross sectional view of a through hole.

Thus, as depicted in model form in FIG. 4, the through hole 22 gradually decreases in cross sectional area due to the upper flat plane 25 approaching the lower flat plane 26 towards the distal end. At the distal end opening 24, the through hole 22 has an opening of generally oval shape. In the present embodiment in particular, viewed in cross section in the direction of extension of the through hole 22, the lower flat plane 26 has a linear contour while the upper flat plane 25 has an arcuate shape of inwardly convex, substantially unchanging curvature across the entire length of the through hole 22 so as to progressively approach the lower flat plane 26 towards the distal end opening 24. Thus, in the present embodiment, the through hole 22 in its entirety defines the tapered portion.

In the insertion tool 10 of the present embodiment, the upper and lower flat planes 25, 26 are formed on the upper and lower planes of the through hole 22, thereby forming flat planes that extend parallel to the center axis of the tool body 12 across the entire length of the nozzle part 20. Additionally, at the connecting sections of the upper and lower flat planes 25, 26 with the left and right wall faces 28, 30 there are formed curved faces of fillet form that extend along the entire length of the through hole 22 and afford smooth interconnection between the upper and lower flat planes 25, 26 and the left and right wall faces 28, 30. As the height dimension of the through hole 22 becomes progressively smaller, the curved faces which have been formed at the upper and lower edges converge together into a single, generally arcuate shape at the distal end side. The distal end opening 24 will thus have a generally oval shape defined by the linear upper and lower flat planes 25, 26 connected in an arcuate shape. The distal end section of the nozzle part 20 is cut on the diagonal so as to taper upward, facilitating insertion into the eye.

Between the nozzle part 20 and the main tubular section 16 in the tool body 12 there is disposed a rest portion 34 provided as a stage for resting the intraocular lens 32. As depicted in model form in FIG. 5A, the rest portion 34 as a whole takes the form of a slot extending in the axial direction and open at the top through an opening 36, the width dimension of the opening 36 being slightly larger than the diameter dimension of the optical portion 38 of the intraocular lens 32. On the transverse opposing faces of the rest portion 34 at a location somewhat below the opening 36 there are formed shoulder portions 40, 40 that jut out towards the center axis of the tool body 12 from both edges in the transverse direction. Thus, the upper faces of the shoulder portions 40, 40 define substantially flat resting faces 41, 41; while between the transverse opposing faces of the shoulder portions 40, 40 there is defined a plunger passage hole 42 provided as a recessed groove of generally "U" shaped cross section open at the top and extending along the center axis of the tool body 12. The plunger passage hole 42 connects at its base face at the distal end to the lower flat plane 26 of the through hole 22 and thereby communicates with the through hole 22.

A cover portion 44 is provided as a cover main body portion to one side (in the present embodiment, the right side) of the rest portion 34 in the tool body 12. The cover portion 44 is integrally formed with the tool body 12 and has dimensions sufficient to cover the rest portion 34 in its entirety, that is, width dimension substantially equal to the width dimension of the tool body 12 and axial length dimension somewhat larger than the maximum length dimension inclusive of the support portions 46, 46 of the intraocular lens 32. The cover portion 44 is formed to have a prescribed thickness dimension, and in its transverse center section the cover portion 44 is perforated in the thickness direction by a guide hole 48 of slit shape extending in the same direction as the axial direction of the tool body 12 across substantially the entire width of the cover portion 44 in the front-back direction.

The cover portion 44 and the tool body 12 are linked by a cover linking portion 50 that has been formed by extending the outside edge portion of the opening 36 in the rest portion 34 outwardly in the transverse direction. The cover linking portion 50 is sufficiently thin to allow the cover portion 44 to bend easily towards the tool body 12, and the cover linking portion 50 constitutes a flexible first linking portion.

A mating piece 52 is formed integrally projecting out from the transverse outside edge of the cover portion 44. Meanwhile, a projecting edge part 54 that projects slightly outward in the transverse direction is formed at the outside edge of the opening 36 on the side opposite from the cover linking portion 50, and a mating notch 56 is formed in the projecting edge part 54, at a location corresponding to the mating piece 52.

A clamping plate member 58 provided as the clamping member is linked by a clamping plate linking portion 60 to the back edge of the cover portion 44. The clamping plate member 58 has a structure integrally incorporating a pedestal portion 62 of generally oblong flat plate shape having planar dimensions slightly smaller than those of the cover portion 44, and a projecting plate portion 64 provided as a clamping projection, that projects from the pedestal portion 62. The projecting plate portion 64 has the shape of a plate extending through the transverse center section of the pedestal portion 62 in the same direction as the axial direction of the tool body 12, with a length dimension extending as far as the optical portion 38 and the support portions 46, 46 of the intraocular lens 32. The projection dimension of the projecting plate portion 64 is slightly larger than the thickness dimension of the cover portion 44. The projecting distal edge of the projecting plate portion 64 is defined by a smoothly curving face that is convex towards the direction of projection.

The clamping plate member 58 is linked to the cover portion 44 by the clamping plate linking portion 60. In the present embodiment, the cover member incorporates the cover portion 44 and the clamping plate member 58. Moreover, in the present embodiment, the cover portion 44, the clamping plate member 58, and the clamping plate linking portion 60 which links them are integrally formed with the tool body 12, with the clamping plate linking portion 60 being produced by imparting a thin plate shape to the segment that connects the cover portion 44 with the clamping plate member 58. The clamping plate linking portion 60 will thereby constitute a segment having sufficient flexibility to allow the clamping plate member 58 to be easily bent towards the cover portion 44 side, with the clamping plate linking portion 60 constituting a flexible second linking portion. Further, in the present embodiment, the clamping plate linking portion 60 has been formed so as to extend in the same direction as the axial direction of the tool body 12 from the back edge of the cover portion 44, while the cover portion 44 and the clamping plate member 58 have been disposed in the same direction as the axial direction of the tool body 12, so that the transverse dimension of the insertion tool 10 may be kept small.

In the present embodiment in particular, the opening 36 of the rest portion 34, the shoulder portions 40, 40, and the plunger passage hole 42 extend with substantially unchanging cross section from the back of the rest portion 34 to the distal end part of the main tubular section 16. In the section of the opening 36 that extends to the rear of the rest portion 34, specifically at the outside edge thereof on the side opposite from the cover portion 44, there is integrally formed a molding-use flap portion 66. Like the cover linking portion 50, the molding-use flap portion 66 is integrally linked to the tool body 12 by a thin, readily bendable molding-use flap linking portion 68 that allows the flap to be opened and closed with respect to the extended section of the opening 36. Also, like the cover portion 44, the molding-use flap portion 66 has a catch piece 70 formed projecting from its outside edge, this catch piece 70 being adapted to hold the flap closed through engagement with an engagement notch 74 that has been formed at a projecting edge part 72 projecting outwardly from the extended section of the opening 36 on the side thereof opposite from the molding-use flap linking portion 68. The molding-use flap portion 66 is provided for the purpose of facilitating molding of the tool body 12 and is not an essential element. Where the molding-use flap portion 66 is omitted, the main tubular section 16, will be formed so as to extend frontward up to the back side of the rest portion 34.

Thus, the tool body 12 in the present embodiment is constituted as a single integrally formed component incorporating the main tubular section 16, the cover portion 44, the clamping plate member 58, and the rest portion 34. The tool body 12 is a transparent member made from light-transmissive material so that even with the rest portion 34 covered by the cover portion 44, the intraocular lens 32 resting on the rest portion 34 will be visible through the cover portion 44 and the clamping plate member 58.

A plunger 14 provided as the plunger member will be inserted from the rear of the tool body 12 having the above structure and passed through the plunger passage hole 42. The plunger 14 is a generally rod-shaped member having a length dimension somewhat larger than the length dimension of the tool body 12 and is provided as an integrally molded component wherein the section lying frontward from the approximately center section in the lengthwise direction defines a working portion 76, the section to the rear defines a guide portion 78, and a back end plate portion 80 of plate shape extending in the axis-perpendicular direction is formed at the back end.

Figure 5A:
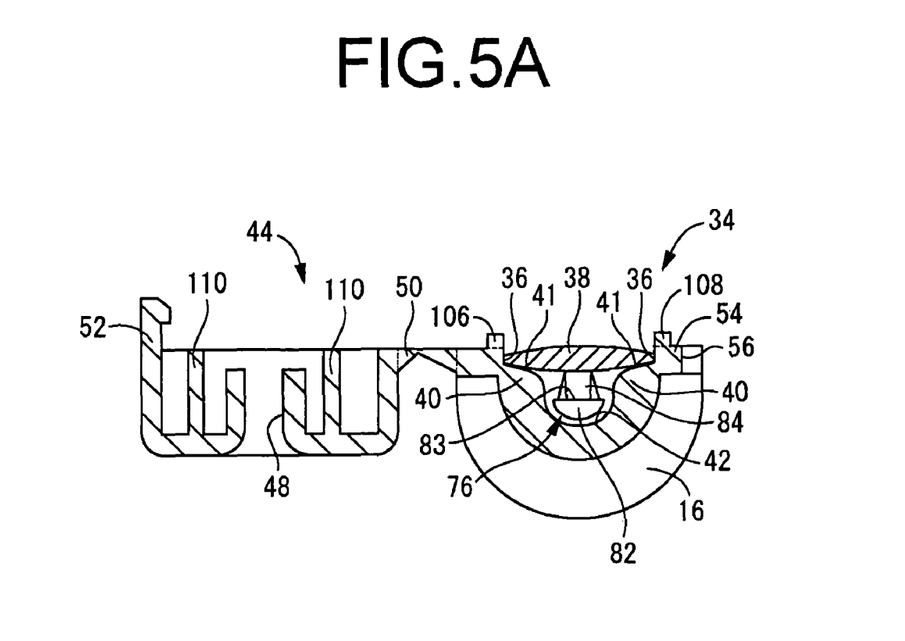
FIG. 5A is a cross sectional view taken along line 5-5 of FIG. 1.
Figure 6:
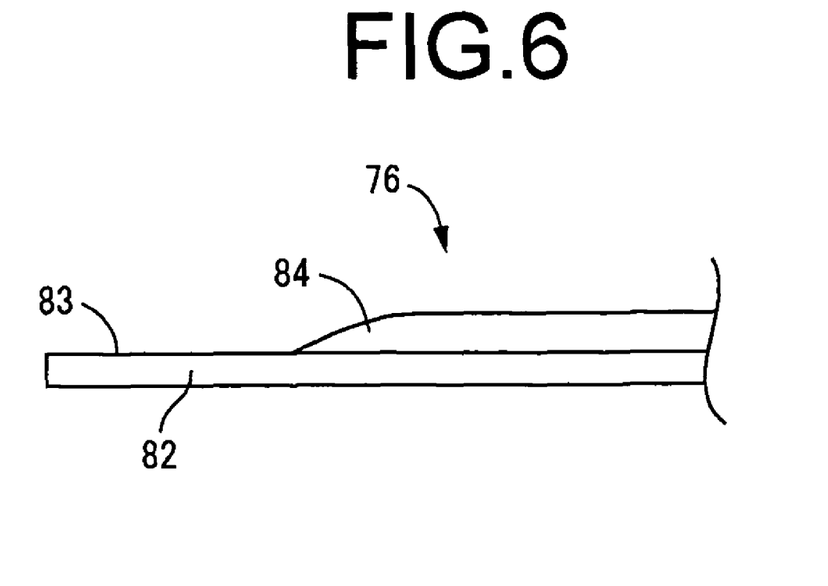
FIG. 6 is a side plane view of a plunger member.

As depicted in FIG. 5A, the working portion 76 has a width dimension such that it can be passed through the plunger passage hole 42 with prescribed clearance. Its distal end portion 82 has a semicircular transverse cross sectional shape on which is formed a flat portion 83 that will be positioned on the upper side when passed through the plunger passage hole 42, and has a substantially unchanging cross section across a prescribed dimension in the axial direction. As depicted in FIG. 6, to the back side of the distal end portion 82 there is formed a sloped portion 84 provided as a plunging guide portion of progressively greater height dimension towards the rear. The segment to the rear of this sloped portion 84 extends in the axial direction with a substantially unchanging cross section. The working portion 76 of the plunger 14 will thereby extend with substantially unchanging semicircular cross section rearward from the distal end at the distal end portion 82, then progressively increase in height and become thicker in the sloped portion 84, then extend with a substantially unchanging cross section from the back end of the sloped portion 84.

The guide portion 78, meanwhile, is formed to the rear of the working portion 76. The guide portion 78 extends in the axial direction with substantially unchanging outside contours of generally oblong shape that is thicker than the working portion 76. In the guide portion 78 there is also formed a recessed guide slot 86 that is open at the top and extends in the axial direction through substantially the entire guide portion 78.

The plunger 14 having the above construction is inserted from the back of the tool body 12, and the working portion 76 is passed through the plunger passage hole 42 of the tool body 12. Here, the shape of the back end opening of the tool body 12 is generally oblong and corresponds to the contours of the guide portion 78, thereby preventing the plunger 14 from rotating with respect of the tool body 12.

In this case, a lock portion 88 has been integrally formed at the back end of the tool body 12. The lock portion 88 includes: an opening 90 that opens at the top of the tool body 12 and communicates with the interior; and a mating flap portion 92 adapted to open and close the opening 90. The mating flap portion 92 is generally plate shaped and integrally formed with the tool body 12, and like the cover linking portion 50 its connecting section with the tool body 12 is thin and deformable so as to allow the flap to open and close the opening 90. A mating piece 94 similar to that of the cover portion 44 is formed at the edge of the mating flap portion 92. The mating flap portion 92 is held in the closed position by engaging the mating piece 94 in a mating notch 96 that has been formed at the edge of the opening 90 on the side thereof opposite from the mating flap portion 92.

A catch projection 100 is formed on the mating flap portion 92 so as to project towards the inside of the tool body 12 in the closed position. The catch projection 100 extends in the axial direction of the tool body 12 and has a width dimension slightly smaller than the width dimension of the guide slot 86. With the mating flap portion 92 in the closed position, it will be positioned within the guide slot 86.

Figure 7:
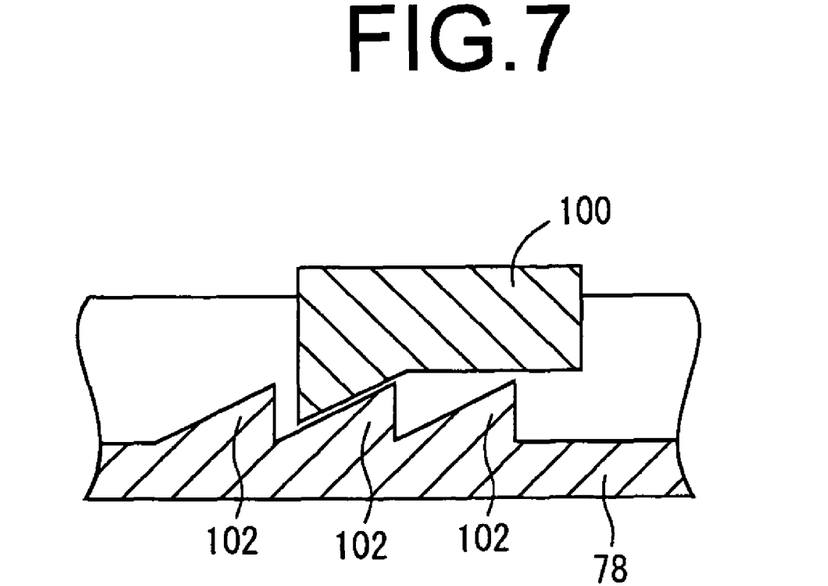
FIG. 7 is a cross sectional view suitable for explaining an advance/retreat prevention mechanism.

Here, as depicted in model form in FIG. 7, on the catch projection 100 a wall face that extends in the plumb vertical direction is formed on the front side edge face, while a sloped face is formed sloping upward towards the rear from the front side edge face. Meanwhile, on the base face of the guide slot 86 at locations in proximity to the front side edge face there are formed a plurality of tooth portions 102, 102 lined up across a prescribed range. The tooth portions 102, 102 at their back end faces define wall faces that extend in the plumb vertical direction and gradually slope downward towards the front from the back end face. Thus, the tooth portions 102, 102 are adapted to interlock at their back end faces with the front side edge face of the catch projection 100 to prevent further displacement rearward with respect to the catch projection 100 while allowing forward relative displacement. This interlocking of the tooth portions 102 with the catch projection 100 also provides a dislodgement-preventing mechanism for preventing displacement of the plunger 14 in the direction of dislodgement from the tool body 12. On the other hand, when the plunger 14 is plunged, the plurality of tooth portions 102 will sequentially engage the catch projection 100, and may thereby be utilized as a regulating mechanism making it possible to plunge the plunger 14 in a regulated fashion. In this way, according to the present embodiment, there is constituted a plunger 14 advance/retreat prevention mechanism that incorporates the catch projection 100 of the lock portion 88 and the tooth portions 102, 102 of the guide slot 86. In FIG. 1, to aid in understanding the mating flap portion 92 is shown open, but as will be apparent from the utilization of the catch projection 100 as a regulating mechanism, in the present embodiment the mating flap portion 92 will be used in the closed position when plunging the plunger 14.

The initial position of the plunger 14 with respect to the tool body 12 is established through interlocking of the catch projection 100 and the tooth portions 102. In the present embodiment in particular, the distal end part of the plunger 14 will be initially positioned at a location situated somewhat to the rear of the optical portion 38 of the intraocular lens 32 which has been rested on the rest portion 34 (the location shown in FIG. 1).

In the insertion tool 10 having the above construction, first, the molding-use flap portion 66 and the mating flap portion 92 will be closed, and with the plunger 14 positioned at the initial position (the location shown in FIG. 1 mentioned above) the intraocular lens 32 will be rested on the resting faces 41, 41 of the rest portion 34. Here, an upwardly projecting positioning projection 104 has been formed to the front of the resting face 41 that is situated towards the cover portion 44 side, and is adapted to position the intraocular lens 32 within the rest portion 34 through the edge of the optical portion 38 of the intraocular lens 32 coming into contact against the back edge of this positioning projection 104.

Figure 8:
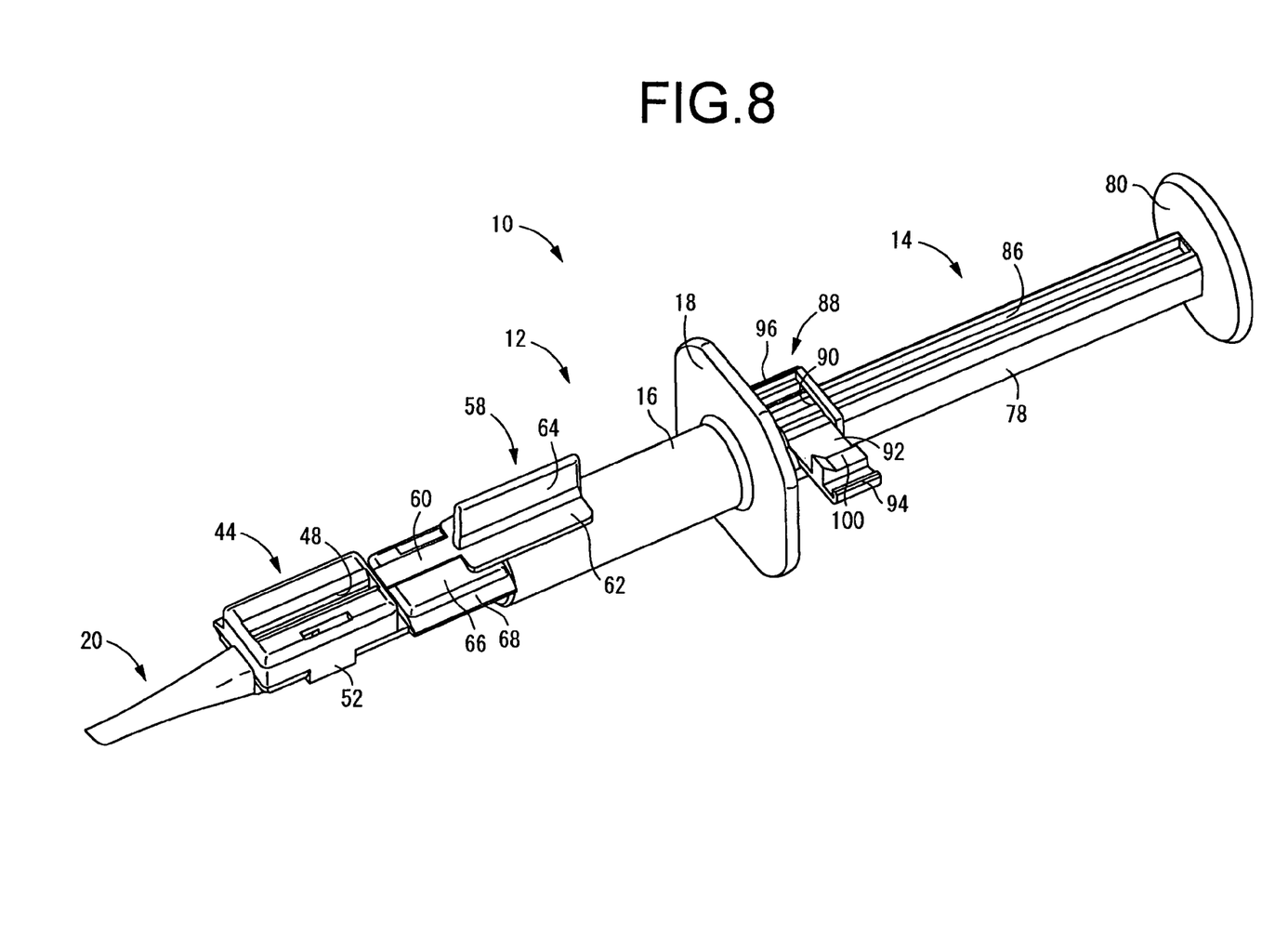
FIG. 8 is a perspective view of the intraocular lens insertion tool in which a cover main body portion is closed.

Then, by bending the cover linking portion 50, the cover portion 44 will be juxtaposed against the opening 36 of the rest portion 34 as depicted in FIG. 8, so that the opening 36 is closed by the cover portion 44. The opening 36 will thereby be provided closure along substantially its entire axial extension by the cover portion 44 and the molding-use flap portion 66. The cover portion 44 is held in the closed position through engagement of the mating piece 52 of the cover portion 44 with the mating notch 56.

Figure 5B:
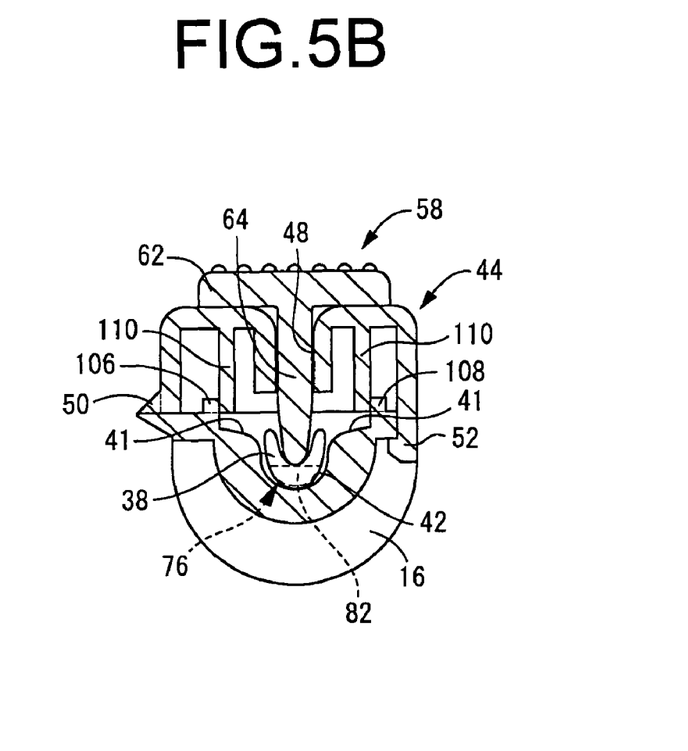
FIG. 5B is a cross sectional view corresponding to FIG. 5A where a cover portion 44 is placed in a closed state.

As depicted in model form in FIG. 5B, at the upper edges of the opening 36 there are formed projecting wall portions 106, 108 that project slightly up and extend across areas of prescribed dimension in the axial direction. The outside faces of guide wall portions 110, 110 that have been formed to either side in the transverse direction of the guide hole 48 of the cover portion 44 will be disposed in contact against the inside faces of the projecting wall portions 106, 108, thereby positioning the cover portion 44 such that the guide hole 48 is situated in the transverse center of the rest portion 34. Positioned thusly, the guide hole 48 of the cover portion 44 will be situated over the center of the optical portion 38 of the intraocular lens 32 resting on the resting faces 41, 41, and will extend along the axial direction of the tool body 12.

Then, with the opening 36 covered by the cover portion 44, by bending the clamping plate linking portion 60 the projecting plate portion 64 will be inserted from above into the guide hole 48 of the cover portion 44 while pushing the projecting plate portion 64 into the tool body 12 until the pedestal portion 62 is detained on the cover portion 44. By so doing, the projecting distal edge of the projecting plate portion 64 will be positioned in contact against the optical portion 38 of the intraocular lens 32, thereby inducing bowing deformation of the intraocular lens 32 to upwardly concave shape while pushing it into the plunger passage hole 42. In the present embodiment, the guide hole 48 is situated extending upward at the center of the intraocular lens 32. The projecting plate portion 64 will be inserted from above into the guide hole 48 with the opening 36 covered by the cover portion 44, whereby the projecting plate portion 64 can be positioned in contact against the intraocular lens 32 from above, and bring about steady bowing deformation. In the present embodiment, this sort of guide means for guiding the projecting plate portion 64 from above the intraocular lens 32 will incorporate the guide hole 48 and the guide wall portions 110, 110. Additionally, because the cover portion 44 and the clamping plate member 58 each have light transmissivity, insertion of the projecting plate portion 64 can be carried out while visually ascertaining the condition of the intraocular lens 32. The guide hole 48 is designed so that its width dimension of the open end situated on the upper side with the opening 36 covered gradually expands in size going upward, thus facilitating insertion of the projecting plate portion 64.

In the present embodiment, the guide hole 48 has a width dimension such that it will flare out slightly upon sliding contact with the projecting plate portion 64, so that the projecting plate portion 64 will be retained in the inserted state through recovery force, frictional force, etc. exerted on the projecting plate portion 64 by the guide hole 48. In the present embodiment, this sort of retaining means for preventing the clamping plate member 58 from becoming dislodged from the cover portion 44 incorporates the wall face of the guide hole 48 and the wall faces of the projecting plate portion 64.

With the intraocular lens 32 bowed in the manner described above, the distal end opening 24 of the nozzle part 20 will be inserted into the eye, and the plunger 14 will be plunged towards the distal end so that the distal end portion 82 of the plunger 14 comes into contact against the optical portion 38 of the intraocular lens 32. In the present embodiment, because the distal end portion 82 of the plunger 14 has a semicircular cross section, in a zone between the projecting plate portion 64 and the plunger passage hole 42, i.e. below the projecting plate portion 64, the distal end portion 82 will come into contact against the optical portion 38 of the intraocular lens 32 without contacting the projecting plate portion 64. It will be possible thereby to push the intraocular lens 32 into the nozzle part 20 while effectively maintaining the lens in a state of deformation by the projecting plate portion 64. Additionally, due to the bowing deformation produced by the projecting plate portion 64, the support portions 46, 46 of the intraocular lens 32 will experience upward displacement so that the distal end portion 82 of the plunger 14 will effectively be prevented from contacting the support portions 46, 46, thereby reducing the risk of damage to the support portions 46, 46.

The intraocular lens 32 that in a deformed state has been pushed into the through hole 22 will experience progressive deformation to smaller size by the through hole 22 as it moves towards the distal end side. In the present embodiment, because the flat upper and lower flat planes 25, 26 have been formed along the entire length of the through hole 22, the intraocular lens 32 will be prevented from rotating in the circumferential direction of the through hole 22. Since the right and left wall faces 28, 30 connect smoothly with the upper and lower flat planes 25, 26, even if the intraocular lens 32 should happen to rotate in the circumferential direction of the through hole 22, it will be possible to avoid a situation where the intraocular lens 32 is subjected to localized high levels of force, thus reducing the risk of unanticipated deformation or damage to the intraocular lens 32.

Further, in the present embodiment, because the sloped portion 84 has been formed on the plunger 14, during plunging of the plunger 14 it will be possible for the plunger 14 to be plunged smoothly by pushing the sloped portion 84 through the plunger passage hole 42 while upwardly displacing the projecting plate portion 64. At the same time, downward force produced by the counteraction exerted on the plunger 14 during pushing of the projecting plate portion 64 will act on the plunger 14 so that its distal end portion 82 can be positioned stably at the base face side of the through hole 22, enabling it to steadily push the intraocular lens 32 into the nozzle part 20. Once transported into the nozzle part 20, the intraocular lens 32 will experience deformation to smaller size by the through hole 22, and will then be pushed out from the insertion tool 10 through the distal end opening 24 of the through hole 22 and inserted into the eye.

In the insertion tool 10 having the above structure, because the rest portion 34 on which the intraocular lens 32 rests is composed of the non-deforming shoulder portions 40, the intraocular lens 32 can be rested easily thereon. With the intraocular lens 32 thusly rested, by covering the opening 36 with the cover portion 44, the intraocular lens 32 can be effectively prevented from popping out or otherwise becoming dislodged.

Additionally, the projecting plate portion 64 can be pushed along under conditions such that the intraocular lens 32 is prevented from becoming dislodged, the intraocular lens 32 can be easily imparted with initial deformation. By pushing the projecting plate portion 64 from above against the center of the intraocular lens 32, initial deformation can steadily be applied to the intraocular lens 32 without inducing rotation.

Further, in present embodiment, because the lower plane of the through hole 22 is defined along its entire length by the lower flat plane 26, once advanced into the through hole 22, the intraocular lens 32 can be positioned clamped steadily against the lower flat plane 26. Because the upper plane which exerts downward clamping force on the intraocular lens 32 also has an upper flat plane 25 that is flat, the intraocular lens 32 can be deformed to smaller size while preventing as practicably as possible the intraocular lens 32 from rotating in the circumferential direction of the through hole 22.

Additionally, in present embodiment, because the left and right wall faces 28, 30 connect smoothly with the upper and lower flat planes 25, 26 in the through hole 22, even if the intraocular lens 32 should happen to rotate in the circumferential direction the through hole 22, localized deformation caused by becoming lodged etc. may be avoided, thus lessening the risk of damage to the intraocular lens 32.

While the invention has been described detail herein in terms of one preferred embodiment, this embodiment is merely exemplary, and the present invention should in no way be construed as limited to the specific disclosure herein.

For example, whereas in the preceding embodiment, the upper flat plane 25 of the through hole 22 approaches the lower flat plane 26 with an arcuate curved portion having substantially unchanging curvature, it is not essential for the through hole 22 to have arcuate shape of substantially unchanging curvature along its entire length. Instead, the curvature could change at an appropriate medial location in the longitudinal direction, as with the through hole 130 depicted in FIG. 9. In the following description, elements that are substantially identical to those in the preceding embodiment are assigned the same symbols as in the embodiment, with no detailed description provided.

Figure 9:
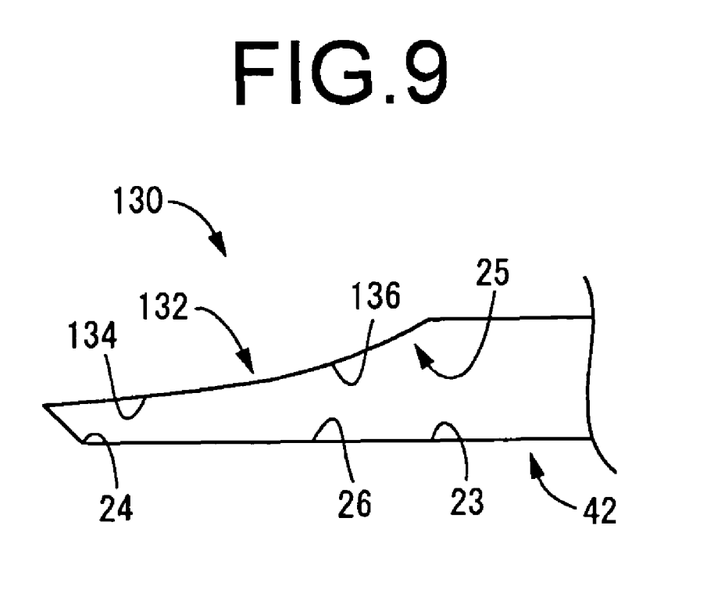
FIG. 9 is a vertical cross sectional view of a through hole of different shape.

In the through hole 130 depicted in FIG. 9, an inflection portion 132 is formed in the generally medial section of the upper flat plane 25 in the front-back direction, with the curvature radius of a frontward upper flat plane 134 that is formed to the front side of the inflection portion 132 viewed in cross section in the direction of extension of the through hole 22 being larger in comparison to the curvature radius of a rearward upper flat plane 136 that is formed to the rear side of the inflection portion 132. With this arrangement, owing to the rearward upper flat plane 136 the intraocular lens will experience rapid deformation in the initial stage of being advanced into the through hole 130, while in the subsequent stage of being advance from the inflection portion 132 to the distal end the lens will experience gradual deformation by the frontward upper flat plane 134. Thus, in the stage in which the intraocular lens has been subjected to initial deformation only and is still able to readily deform, rapid deformation of the lens to shorter dimension in the front-back direction can be brought about by the rearward upper flat plane 136, and the overall length of the insertion tube can be made shorter.

Figure 10:
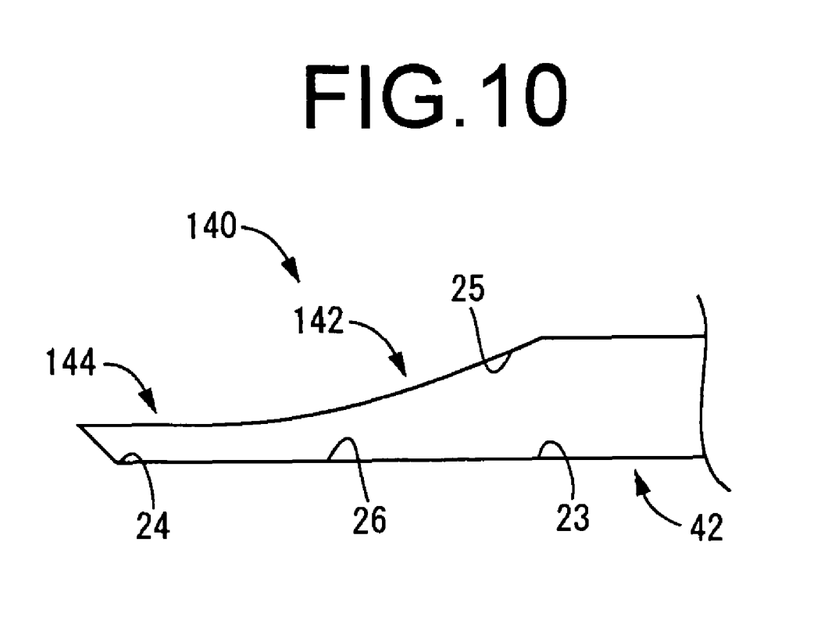
FIG. 10 is a vertical cross sectional view of a through hole of another different shape.

While the through holes 22, 130 in the preceding embodiments are each formed with a tapered portion along the entire length, it would also be acceptable for a straight portion 144 to be formed extending with substantially unchanging cross section towards the distal end opening 24 from the distal end part of a tapered portion 142, as with the through hole 140 depicted in FIG. 10. Furthermore, it is not essential for the tapered portion to be formed starting from the proximal end portion of the insertion tube, and it could instead be formed at a medial location in the longitudinal direction of the insertion tube.

The insertion tube having the specific shape in accordance with the present invention may be implemented in any of various insertion tools known in the art, such as an insertion tool adapted to deform the intraocular lens while it rests on a reclosable hinge portion as taught in Japanese Domestic Publication of International Patent Application Nos. 2002-525023 and 11-506357 cited earlier, for example.

The plunger 14 provided as the plunger member in the preceding embodiment is merely exemplary and other modes may be advantageously employed, for example, one in which a readily deformable flexible member adapted to contact the intraocular lens is disposed at the distal end portion of the plunger member.

Figure 11:
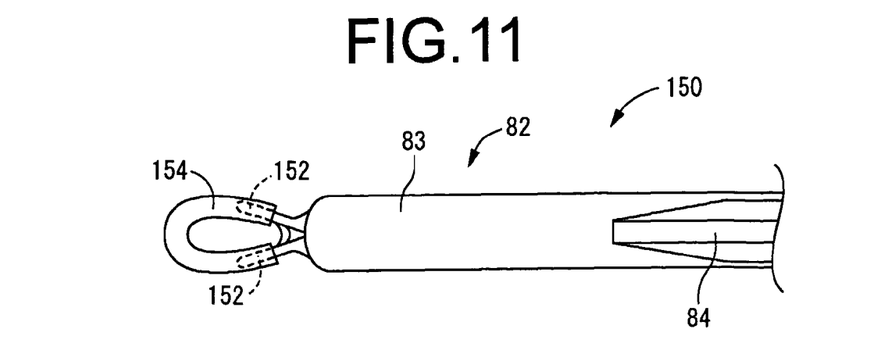
FIG. 11 is a top plane view of a plunger member of different shape.

FIG. 11 depicts a plunger 150 by way of one mode of a plunger member provided with such a structure. The plunger 150 includes a pair of branched portions 152, 152 integrally formed at the distal edge of the distal end portion 82 and branching into generally "Y" shape towards the distal end direction. A tube 154 provided as the flexible member is attached to the branched portions 152, 152 in a bowed loop configuration between them. The tube 154 will have for example a hollow, round tubular shape made of readily deformable flexible material such as rubber, and will be attached at the distal edge part of the distal end portion 82 by slipping its two ends onto the outside of the branched portions 152, 152. Here, because only the ends of the tube 154 are slipped externally onto the branched portions 152, 152, its lengthwise medial section situated at the very tip of the plunger 150 will be readily deformable.

With this arrangement, when pushing the intraocular lens 32, the readily deformable tube 154 will come into contact against the intraocular lens 32, thereby reducing excessive force on the intraocular lens 32 and reducing the risk of damage or breakage of the intraocular lens 32 as it is pushed along. It will also be possible to advantageously accommodate and conform to shape changes occurring between the proximal end opening 23 and the distal end opening 24 of the through hole 22 having specific shape like that taught in the present invention.

The plunger 150 constructed in accordance with this mode will afford more effective benefits when a lubricant is injected into the rest portion 34 or through hole 22 to enable pushing of the intraocular lens 32 to take place smoothly. Specifically, because the tube 154 has the form of a readily deformable loop, its pushing force can be directed through a wide range of the intraocular lens 32 via the lubricant, making it possible for the lens to be pushed more smoothly and steadily.

Figure 12:
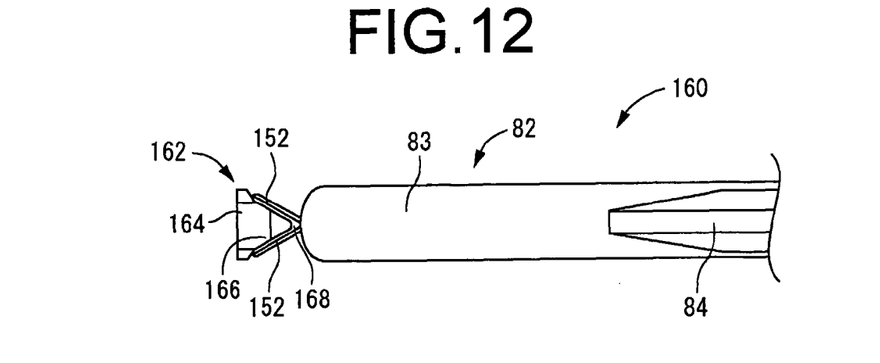
FIG. 12 is a top plane view of a plunger member of another different shape.

A plunger 160 according to yet another mode of a plunger member furnished with a flexible member is depicted in FIG. 12. Like the plunger 150 described above, the plunger 160 has a pair of branched portions 152, 152 integrally formed at the distal edge of its distal end portion 82 and branching into generally "Y" shape towards the distal end direction. A working member 162 provided as the flexible member is disposed between the opposing faces of the branched portions 152, 152. The working member 162 is made of readily deformable, elastic material such as rubber or silicone for example, with the width dimension of its front edge portion 164 being approximately equal to the width dimension of the through hole 22, and the width dimension of its back edge portion 166 being equal to the distance separating the branched portions 152, 152 at a medial location in the axial direction of the plunger 160. The working member 162 will thereby be clasped between the branched portions 152, 152 at the side edges of a zone in proximity to its back edge portion 166 and positioned at the tip section of the plunger 160. The working member 162 may be disposed fixedly on the branched portions 152, 152 with adhesive or the like, or disposed non-fixedly. The front edge portion 164 of the working member 162 will project out somewhat beyond the distal end sections of the branched portions 152, 152. A gap of appropriate size is formed between the back edge portion 166 and the proximal end portion 168 of the branched portions 152, 152. According to this mode, as with the plunger 150 described previously, by positioning the working member 162 in cushioned contact against the intraocular lens 32 the risk of damage to the intraocular lens 32 will be reduced, and pushing of the intraocular lens 32 can take place in a more steady manner when a lubricant is injected.

It hardly bears a mention that the specific structure of the flexible member is not limited to the modes described above. For example, the tube 154 of the plunger 150 described above could be bent at the distal end sections of the branched portions 152, 152 to produce a generally triangular shape in top view. By so doing, the segment of the tube 154 situated closest to the distal end of the plunger 150 can take the form of a straight line connecting the branched portions 152, 152, in other words, a straight line extending substantially all the way across the width of the through hole 22. The tube 154 can thus come into contact with the intraocular lens 32 over a wider range, so that pushing can take place more steadily.

Figure 13:
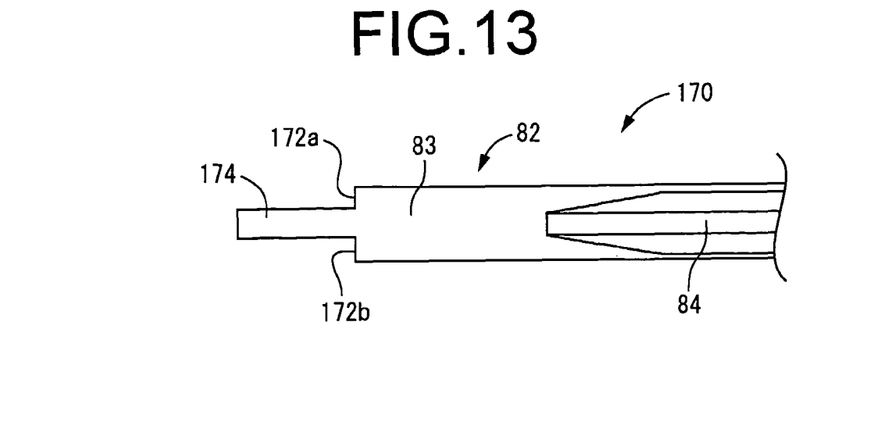
FIG. 13 is a top plane view of a plunger member of further different shape.

Furthermore, the distal end section of the plunger member may be provided with notches for the purpose of producing a prescribed gap between the insertion tube and the plunger member. A plunger 170 according to one mode of a plunger member furnished with such a construction is depicted in FIG. 13. In the present mode, the plunger 170 on both transverse sides of its distal end portion 82 is cut away across areas of prescribed dimension extending axially rearward from the distal edge, thereby producing notches 172a, 172b on both transverse sides of its distal end portion 82. A contact portion 174 is formed between the notches 172a, 172b. The axis-perpendicular dimension of the notches 172a, 172b will be approximately one-fourth the width dimension of the distal end portion 82.

As the plunger 170 having the above structure pushes the intraocular lens 32 along, the distal edge of the contact portion 174 will be positioned in contact with the optical portion 38 of the intraocular lens 32. In the plunger 170 according to the present embodiment, owing to the presence of the notches 172a, 172b, gaps will be produced between the contact portion 174 and the plunger passage hole 42 or through hole 22, and as the intraocular lens 32 experiences deformation as it is pushed along, its support portions 46 can be positioned within these gaps. The risk of the support portions 46 becoming damaged due to being pinched between the plunger 170 and the plunger passage hole 42 or through hole 22 can be reduced as a result.

The specific contours of the notches in the plunger 170 described above are merely exemplary and may be established appropriately in consideration of factors such as the shape of the through hole 22 which guides the intraocular lens 32, the condition of deformation of the intraocular lens 32, and so on. For example, a notch that opens upwardly could be formed at the distal end part of the plunger member.

In the preceding embodiments, the intraocular lens 32 is depicted by way of example as an intraocular lens having support portions 46 of leg form extending out from the optical portion 38. However, the intraocular lens insertion tool of the present invention is adaptable for use with intraocular lenses of any of the designs to date furnished with support members of plate form.

While not described one by one herein, other embodiments arrived at through various modifications, alterations, or improvements of the present invention will be apparent to the practitioner and as such, as a matter of course, shall lie within the true spirit and scope of this invention.

The invention claimed is:

1. An intraocular lens insertion tool including a tool body having a generally tubular shape for accommodating an intraocular lens, and a plunging member inserted into the tool body from a rear in an axial direction and moved forward for inserting into an eye the intraocular lens such that the intraocular lens undergoes compact deformation during forward displacement in the axial direction by the plunging member and is pushed out, wherein an insertion tube disposed at a distal end section of the tool body and adapted for insertion into the eye, viewed perpendicular to a direction of extension thereof, has across an entire length from a proximal end opening, which is adjacent to and in contact with a stage arranged on which the intraocular lens rests, to a distal end opening of the insertion tube a cross section, wherein upper and lower portions have traverse linear portions that extend substantially parallel in a width direction, left and right portions connect smoothly with the upper and lower portions, the left and right portions, in at least one part of the insertion tube in the direction of extension towards the proximal end opening, have longitudinal linear portions that extend substantially parallel in a vertical direction, and the left and right portions gradually curve in an inwardly concave direction at a progressively smaller curvature radius toward the distal end opening so that the upper and lower portions gradually approach one another to form a tapered portion having a reduced cross-sectional area, thus producing the distal end opening of substantially oval shape.

2. The intraocular lens insertion tool according to claim 1, wherein the cross section of the insertion tube viewed perpendicular to the direction of extension will become gradually smaller towards the tapered portion across the entire length from the proximal end opening to the distal end opening of the insertion tube, so that the tapered portion is formed across the entire length of the insertion tube.

3. The intraocular lens insertion tool according to claim 1, wherein as viewed in cross section in a direction of extension, the lower portion of the tapered portion has a linear shape, whereas the upper portion of the tapered portion has an inwardly convex, arcuate curved portion of substantially unchanging curvature which gradually approaches the lower portion of the tapered portion towards the distal end opening.

4. The intraocular lens insertion tool according to claim 1, the stage is positioned at approximately a center section in the axial direction of the tool body, the stage being open at a top and adapted for the intraocular lens to rest thereon, an upwardly open recessed groove is formed on the stage so as to extend in the axial direction of the insertion tube and communicates with the proximal end opening, and a cover member is provided to close an opening of the stage, and has a clamping projection adapted to clamp the intraocular lens resting on the stage from above and to compress the intraocular lens into the recessed groove in an upwardly concave curved state so that the intraocular lens is pushed in a curved state into the insertion tube.

5. The intraocular lens insertion tool according to claim 4, wherein the plunging member has a plunging guide portion adapted to contact against and push the clamping projection upward during plunging of the plunging member.

6. The intraocular lens insertion tool according to claim 1, wherein the distal end opening of the insertion tube is cut on a diagonal so as to taper upward where the upper portion is located.

* * * * *